United States Patent [19]

Young

[11] 4,028,196
[45] June 7, 1977

[54] PH RESPONSIVE GLASS COMPOSITIONS AND ELECTRODES

[75] Inventor: Chung-Chang Young, Toledo, Ohio

[73] Assignee: Owens-Illinois, Inc., Toledo, Ohio

[22] Filed: June 19, 1975

[21] Appl. No.: 588,446

[52] U.S. Cl. .......................... 204/1 T; 204/195 G; 106/52

[51] Int. Cl.² ...................................... G01N 27/36

[58] Field of Search .............. 204/1 T, 1 H, 195 G; 106/52

[56] References Cited

UNITED STATES PATENTS

| | | | |
|---|---|---|---|
| 2,444,845 | 7/1948 | Perley | 204/195 G |
| 2,462,843 | 3/1949 | Cary et al. | 106/52 |
| 2,497,235 | 2/1950 | Perley | 204/195 G |
| 2,668,143 | 2/1954 | Gilbert et al. | 204/195 G |
| 3,372,104 | 3/1968 | Ross et al. | 106/52 |
| 3,410,777 | 11/1968 | Ross | 204/1 H |
| 3,451,830 | 6/1969 | Nishimoto et al. | 204/195 G |
| 3,458,422 | 7/1969 | Proctor | 204/195 G |
| 3,480,536 | 11/1969 | Arthur | 204/195 G |
| 3,713,992 | 1/1973 | Akazawa | 204/1 H |

Primary Examiner—T. Tung
Attorney, Agent, or Firm—Richard B. Dence; Alan J. Steger; Howard G. Bruss

[57] ABSTRACT

Disclosed are pH responsive glass compositions which contain specified proportions of $LiO_2$, $SiO_2$, $La_2O_3$, and $Ta_2O_5$. In some embodiments, the glasses also contain a small proportion of $Cs_2O$. The glasses have very low electrical resistivity, are stable against devitrification, and are readily melted and formed into shapes which are suitable for glass electrodes.

26 Claims, 1 Drawing Figure

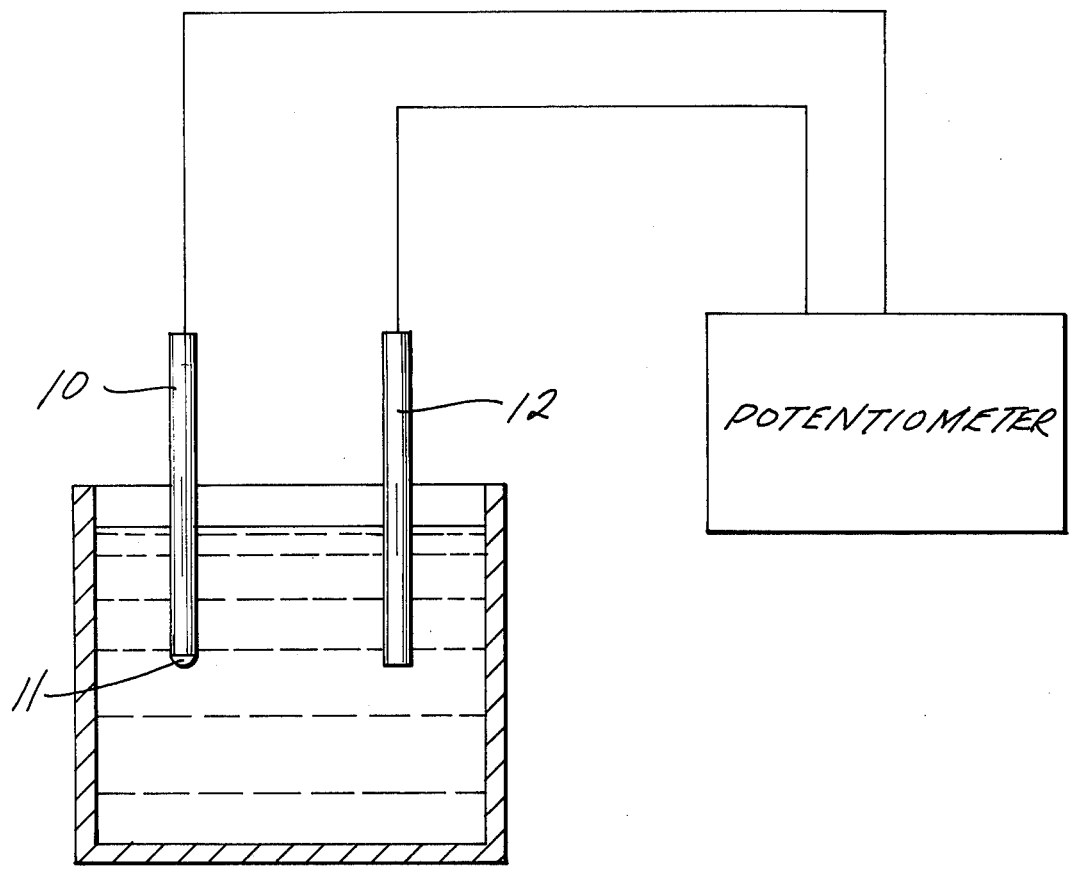

PH RESPONSIVE GLASS COMPOSITIONS AND ELECTRODES

There has been a great deal of research directed toward the development of compositions for use in glass electrodes for pH measurement and potentiometric applications. Such glass electrodes are widely used in the scientific laboratory, as well as in many industrial and medical applications.

The "ideal" glass composition for electrode applications would have very low electrical resistance, no deviation from Nerstian response, no deviation in response due to the presence of sodium and other cations (i.e. sodium error), and high chemical durability. Low electrical resistance is important in minimizing errors due to electrical leakage, IR drop errors due to loading of the amplifier and electrostatic interference. In addition to these properties the ideal glass must have a composition that is readily melted, refined, and formed to the desired electrode size and shape without devitrification or phase separation. It is known that such devitrification has a detrimental effect on the electrical properties.

Glass electrodes presently available represent a compromise between these properties but have not achieved the combination of low electrical resistivity and stability against devitrification. For instance, compositions with very low electrical resistivity usually exhibit poor chemical durability and easily devitrify during forming. Sodium error, while being important for measurements at high pH values in the 11–14 range, is not a significant factor at low and intermediate pH values.

In the past a wide variety of glass compositions in the systems including sodium oxide-calcium oxide-silica; lithium oxide-barium oxide-silica; lithium oxide-barium oxide-lanthanum oxide-silica; and lithium oxide-cesium oxide-lanthanum oxide-silica have been proposed for use in pH responsive electrodes as reported in Analytical Chemistry Vol. 21, pp. 394–401, (1949) and U.S. Pat. Nos. 2,444,845; 2,497,235; 2,668,143; 3,451,830; and 3,238,050. More recently U.S. Pat. Nos. 3,372,104 and 3,410,777 have proposed lithium oxide-cesium oxide-lanthum oxide-silica glasses containing selected quantities of tantalum and/or uranium oxides.

Despite these developments there is a present need for glass compositions suitable for use in pH electrodes which exhibit Nerstian response and have low electrical resistivity are readily formed without devitrification.

Accordingly, it is an object of the present invention to provide pH responsive glass compositions which exhibit Nerstian or near Nerstian response, have electrical volume resistivity below about $10^{10}$ ohm-cm and preferrably below about $10^9$ ohm-cm at room temperature, have relatively low sodium error, are stable against devitrification and are readily melted and formed in shapes suitable for use in glass electrodes.

In attaining the objects of this invention, one feature resides in a pH responsive glass composition consisting essentially of:

| Component | Mole % |
|---|---|
| $Li_2O$ | 30–40 |
| $SiO_2$ | 50–60 |
| $La_2O_3$ | 2–8 |
| $Ta_2O_5$ | 2–8 |
| $Cs_2O$ | 0–3 |
| wherein $Li_2O+Ta_2O_5$ | $\geq 34$ |

For efficiency in use and economy in manufacture, the glass compositions consist essentially of:

| Component | Mole % |
|---|---|
| $Li_2O$ | 32–36 |
| $SiO_2$ | 55–59 |
| $La_2O_3$ | 4–7 |
| $Ta_2O_5$ | 4–7 |

In either of the composition ranges set forth above, the glasses can contain $Cs_2O$ which when present, is usually present in the range of 1–3%. The incorporation of cesium oxide is believed to decrease the sodium error and can be deleted from those glasses for electrodes where sodium error is not a factor. $Cs_2O$ has a tendency to increase the electrical resistivity so its proportion is held below about 3%. Lanthanum oxide appears to lower electrical resistivity and improve stability of the glass while also decreasing sodium error. One of the primary features of the present invention is the use of increased proportions of $Li_2O$ and increased proportions of $Ta_2O_5$ for the combined properties of lower electrical resistivity and stability. In this regard it has been empirically determined that the combined content of $Li_2O + Ta_2O_5$ should be at least 34% to achieve these results.

The use of lithium oxide rather than sodium oxide or potassium oxide has been previously recognized as an approach to pH glasses having reduced sodium errors. For instance, a glass containing $Li_2O$ (27%) - $BaO$(5.5%) - $La_2O_3$(4.5%) - $SiO_2$(63%) has been proposed, but this glass has a log volume resistivity of 11, which is more than one order of magnitude more resistive than those glasses of the present invention.

Another prior art lithium silicate glass system is one containing cesium oxide and lanthanum oxide. A particular glass in this field (see U.S. Pat. No. 3,410,777) consists essentially of: $Li_2O$(27%) - $Cs_2O$(4%) - $La_2O_3$(7%) - $SiO_2$(62%) which has log volume resistivity of 11.16.

Tantalum oxide as a constituent of pH glasses is suggested in U.S. Pat. No. 2,444,845, but is disclosed only as one component in a lithia-silica glass comprising also one or more of the oxides CaO, BaO, and SrO. U.S. Pat. No. 2,497,235 glass compositions are broadly disclosed which can include tantalum oxide. U.S. Pat. No. 3,371,104 discloses the use of uranium and/or tantalum oxides as additives to pH glass compositions in the $Li_2O-Cs_2O-SiO_2-La_2O_3$ system. The tantalum oxide content is contemplated as being in the range of 1–3 mole percent. Specific glass compositions disclosed in this patent with the corresponding log volume resistivity and sodium error values are presented for the purposes of comparison in the Examples. This comparison shows that these glasses of the prior art have higher electrical resistivities as compared to those glasses of the present invention. Thus the prior art has recognized the use of lithium oxide in pH responsive glass compositions, but has not provided a stable glass with the low electrical resistivities accomplished by the present invention. One of the factors responsible for this improvement is the use of $Ta_2O_5 + Li_2O$ in the higher proportions than is suggested in the art together with stabilizing proportions of other oxides.

In contrast to glasses of the prior art, the glass compositions of the present invention incorporate $Li_2O$ in at least 30 mole percent together with $Ta_2O_5$ such that $Li_2O+Ta_2O_5$  34% and $SiO_2$ at no more than 60 mole percent. The unexpected stability achieved in the compositions of invention are not presently understood although it may be due in part to the presence of higher than usual amounts of lanthanum and tantalum oxides, in the indicated proportions. While it is believed that both oxides contribute to the stability of the glasses, it appears that when lanthanum oxide is the major and tantalum oxide the minor component the sodium error is minimized, but the electrical resistivity increases. Conversely when tantalum oxide is the major and lanthanum oxide the minor component the electrical resistivity is minimized at the expense of an increased sodium error. In many applications in the absence of sodium or at low to intermediate pH ranges, the sodium error is not a factor. The preferred composition range has lanthanum oxide and tantalum oxide in approximately equal molar amounts.

The method for melting and refining the glass compositions of invention are well established in the art and no unusual techniques are required. Suffice it to say that conventional high parity (e.g. reagent grade) batch materials are usually melted in refractory vessels such as platinum to minimize the concentration of undesirable impurities. Electric or gas fired melting in an air atmosphere at temperatures in the range of 1350° C–1700° C is quite satisfactory.

The glass compositions described above can be used as the glass sensing membrane of any practical shape and design in the so-called "glass electrode". For instance, glass electrodes having a bulbous sensing membrane as disclosed in U.S. Pat. No. 2,809,090 or 3,649,505 can be formed; glass electrodes having disc shaped sensing membrane as disclosed in U.S. Pat. No. 3,806,440 can be formed; or a wide variety of other shapes and sizes of sensing membranes such as disclosed in U.S. Pat. No. 2,756,203 or the test "Electrometric ph Determinations" by Roger G. Bates (John Wiley & Sons, Inc. New York) can be employed. The term "sensing membrane" is used herein consistent with its usage in potentiometric electrode technology, and is intended to embrace a flat, bulbous or other curved electrode tip, which provides a pair of surfaces between which charge transfer is affected. The technique for calibration and pH measurement using the electrodes of the present invention are well established in the art such as described in the patents and publications mentioned above.

The use of disc shaped membranes is particularly suitable for glass compositions of invention for direct fusion sealing to conventional stem glass compositions. Thus, pH glasses can be melted, cast as a billet in a mold and core drilled to produce rods, and the rods sliced into wafers of suitable thickness. The wafers can be ground and polished after fusing to a stem glass to provide a pH responsive flat glass electrode.

Other objectives and features of the present invention will become apparent from the following description taken in conjunction with the drawing which is a schematic representative of equipment for use in practicing the present invention.

Referring now to the drawing conventional equipment is illustrated for measuring pH employing one embodiment of an otherwise conventional glass electrode 10 with a sensing membrane 11 made of a glass composition of invention. The glass electrode 10 is electrically connected to a standard half-cell electrode 12, such as saturated KCl calomel, or silver-silver chloride electrode by means of a high impedance, potentiometer such as a conventional laboratory "pH meter" as described in the Bates test described above. Electrodes 11 and 12 are shown as being immersed in a vessel of aqueous test specimen.

The potentiometer can be calibrated with standard aqueous buffer solutions containing known concentrations of hydrogen ion as is well-known in the art, and then the $H^+$ concentration of unknown solutions can be determined directly by subjecting the calibrated glass electrode and reference electrode to the unknown solutions according to the usual procedure.

Details of the preparation and use of glass compositions and electrodes of invention are set forth in the following examples. Unless otherwise stated, all percentages are mole percentages and all temperatures are in °C throughout the specification and claims.

EXAMPLE 1

A glass having the following composition:

| Component | Mole % |
| --- | --- |
| $SiO_2$ | 55 |
| $Li_2O$ | 34 |
| $Cs_2O$ | 1 |
| $La_2O_3$ | 5 |
| $Ta_2O_5$ | 5 | is prepared by melting appropriate proportions of the reagent grade batch materials silica, lithium carbonate, cesium carbonate, lanthanum oxide, and tantalum pentoxide in a platinum vessel, in an electric furnace under an air atmosphere at a temperature of 1370° C for 4 hours to form a homogeneous seed-free, batch-free, molten glass. The molten glass is occasionally stirred during melting.

After melting, the molten glass is poured and formed into a slab in a steel mold and annealed at 550° for one hour and then cooled to room temperature. The resulting glass has an Annealing Point of 530° C and a Strain Point of 496° C.

A glass electrode is prepared by remelting the above glass and dipping a chemically and electrically inert "stem" glass tube into the molten glass to collect a glass sensing membrane on the end of the stem glass. Conventional stem glasses are known in the art for this purpose. The sensing membrane is about 30–80 mils in thickness. The stem glass is a thin walled tube having an outside diameter of about 8 mm and an inside diameter of about 6 mm. The glass of invention is stable against devitrification during forming.

The resulting glass electrode is filled with a pH 7 phosphate buffer solution which is 0.1 N in sodium chloride and a Ag/AgCl electrode is immersed in it. The assembled electrode is connected to a conventional high impedance electrometer, (a Model 610R electrometer manufactured by Keithley Instruments, Inc.), along with a standard silver/silver chloride reference electrode. The test electrode and reference electrode are immersed in a 0.1 N hydrochloric acid solution. The potential (i.e. the EMF) of this cell is measured. A known standard resistance is then connected across the electrode leads and the potential again recorded. The resistance of the test electrode is calculated from the equation $$Re = R_s \left( \frac{E_1}{E_2} - 1 \right)$$

wherein $Re$ is the resistance of of the test electrode, $R_s$ the standard resistance and $E_1$ and $E_2$ the EMF measurements for the test cell and the cell with known resistance. The resistance of the test electrode is essentially equivalent to the resistance of the glass membrane.

This procedure for the determination of glass electrode resistance is generally described in the Bulletin Al 1.1 published by the Scientific Apparatus Makers Association, SAMA, Washington, D. C. (1974).

The volume resistivity of the sensing membrane in the pH electrode is calculated from the equation:

$$R_e = \frac{\rho l}{A}$$

wherein $R_e$, as above, is the resistance of the electrode, $l$ the membrane thickness, $A$ the membrane area, and $\rho$, rho, is the volume resistivity. Using this equation the volume resistivity of the above electrode is found to be $4 \times 10^8$ ohm-cm or expressed logarithmically, 8.6.

The electrode potential is observed to change 171 millivolts when the test electrode and reference electrodes are immersed in standard NBS (National Bureau of Standards) buffer solutions of pH 4.0 and 7.0. This corresponds to 57 mv/pH unit which is quite close to Nerstian response.

The sodium error of the above electrode is determined by measuring the millivolt response of the electrode in a 0.1 N sodium hydroxide solution at room temperature. The reading of the electrode is 0.2 pH units below theoretical. Thus the sodium error is 0.2 pH units of 12 millivolts.

EXAMPLE 2

The appropriate amounts of lithium carbonate, silica, lanthanum oxide, and tantalum pentoxide are melted as in Example 1 at 1370° under an air atmosphere for six hours to produce a glass composition consisting essentially of:

| Component | Mole % |
|---|---|
| $SiO_2$ | 56 |
| $Li_2O$ | 33 |
| $La_2O_3$ | 5 |
| $Ta_2O_5$ | 6 |

The glass is manually stirred periodically and poured into a steel mold where it is annealed at 540° for one hour and cooled to room temperature.

A glass electrode is prepared as described in Example 1 and the volume resistivity is measured to be $2 \times 10^8$ ohm-cm of log $\rho = 8.30$. The glass of invention is stable against devitrification during forming. The sodium error is measured as in Example 1 and is determined to be 0.30 pH units or 18 mv. The electrode exhibits Nerstian response and exhibits a pH response of 59.1 millivolts per pH unit between pH 4.0 and 7.0.

Several additional exemplary compositions are prepared and evaluated as above. The compositions and properties for these glasses are set forth in Table 1. All of the glasses of invention are readily melted and refined and are stable against devitrification during forming.

As can be seen from the foregoing data, the glasses of invention have lower electrical resistivity than have been achieved by the prior art. The log volume resistivities are in the range of 8.3 to 9.5 ohm-cm, (only Example 11 containing $Li_2O + Ta_2O_5 = 36$ being in excess of 9) while sodium errors are 0.2 to 1.0 pH unit or 12 to 59 millivolts.

For convenience in disclosure all patents and publications mentioned herein are incorporated by reference.

| Example | 3 | 4 | 5 | 6 | 7 | 8 | 9 | 10 | 11 | 12 | 13 | 14 |
|---|---|---|---|---|---|---|---|---|---|---|---|---|
| Component | | | | | | | | | | | | |
| $SiO_2$ | 60 | 57 | 56 | 55 | 55 | 55 | 59 | 56 | 55 | 55 | 55 | 50 |
| $Li_2O$ | 30 | 32 | 33 | 34 | 34 | 34 | 30 | 33 | 34 | 34 | 34 | 40 |
| $La_2O_3$ | 4 | 5 | 4 | 6 | 5 | 4 | 6 | 6 | 8 | 2 | 3 | 5 |
| $Ta_2O_5$ | 6 | 6 | 7 | 5 | 6 | 7 | 4 | 4 | 2 | 8 | 5 | 4 |
| $Cs_2O$ | 0 | 0 | 0 | 0 | 0 | 0 | 1 | 1 | 1 | 1 | 3 | 1 |
| Properties | | | | | | | | | | | | |
| Log volume resistivity at 25° C (ohm-cm) | 8.9 | 8.5 | 8.5 | 8.8 | 8.3 | 8.3 | 8.9 | 8.5 | 9.5 | 8.3 | 8.9 | 8.3 |
| Sodium error (mv) at 25° C | 59 | 40 | 59 | 12 | 12 | 59 | 25 | 18 | 18 | 59 | 45 | 65 |

| Example | Control 1 | Control 2 | Control 3 |
|---|---|---|---|
| Component | | | |
| $SiO_2$ | 62 | 63 | 60 |
| $Li_2O$ | 27 | 27 | 27 |
| $La_2O_3$ | 7 | 4 | 7 |
| $Ta_2O_5$ | 2 | 2 | 2 |
| $Cs_2O$ | 2 | 4 | 4 |
| Properties | | | |
| Log volume resistivity at 25° C (ohm-cm) | 10.1 | 10.27 | 10.91 |
| Sodium error (mv) at 25° C | 10 | 2 | < 10 |

Having thus described the invention, what is claimed is:

1. A glass composition for use in pH responsive glass electrodes consisting essentially of:

| Component | Mole % |
|---|---|
| $Li_2O$ | 30–40 |

-continued

| Component | Mole % |
| --- | --- |
| $SiO_2$ | 50–60 |
| $La_2O_3$ | 2–8 |
| $Ta_2O_5$ | 2–8 |
| $Cs_2O$ | 0–3 |
| wherein $Li_2O+Ta_2O_5$ | ≥34 |

2. The glass composition of claim 1 consisting essentially of:

| Component | Mole % |
| --- | --- |
| $Li_2O$ | 32–36 |
| $SiO_2$ | 55–59 |
| $La_2O_3$ | 4–7 |
| $Ta_2O_5$ | 4–7 |

3. The glass composition of claim 1 which contains at least 1 mole % $Cs_2O$.

4. In a glass electrode for pH and potentiometric measurements, the improvement wherein the glass sensing membrane of said electrode has a composition of claim 1.

5. In a glass electrode for pH and potentiometric measurements, the improvement wherein the glass sensing membrane of said electrode has a composition of claim 2.

6. In the process for measuring the pH of an aqueous solution, wherein a glass electrode is contacted with said solution and the resulting potentiometric response is a measure of the hydrogen ion concentration of said solution, the improvement wherein said glass electrode is the electrode of claim 4.

7. In the process for measuring the pH of an aqueous solution which process includes the steps of providing an electrode with a pH responsive glass sensing membrane, immersing said sensing membrane and a standard reference electrode in said solution while said glass electrode and said reference electrode are electrically connected to a potentiometer, the improvement wherein said ion selective glass sensing membrane has a composition of claim 5.

8. In the process for measuring the pH of an aqueous solution which process includes the steps of providing an electrode with a pH responsive glass sensing membrane, immersing said sensing membrane and a standard reference electrode in said solution while said glass electrode and said reference electrode are electrically connected to a potentiometer, the improvement wherein said ion selective glass sensing membrane has a composition of claim 4.

9. The glass composition of claim 1 consisting essentially of:

| Component | Mole % |
| --- | --- |
| $Li_2O$ | 30 |
| $SiO_2$ | 60 |
| $La_2O_3$ | 4 |
| $Ta_2O_5$ | 6 |

10. The glass composition of claim 1 consisting essentially of:

| Component | Mole % |
| --- | --- |
| $Li_2O$ | 30 |
| $SiO_2$ | 59 |
| $La_2O_3$ | 6 |
| $Ta_2O_5$ | 4 |
| $Cs_2O$ | 1 |

11. The glass composition of claim 1 consisting essentially of:

| Component | Mole % |
| --- | --- |
| $Li_2O$ | 34 |
| $SiO_2$ | 55 |
| $La_2O_3$ | 8 |
| $Ta_2O_5$ | 2 |
| $Cs_2O$ | 1 |

12. The glass composition of claim 1 consisting essentially of:

| Component | Mole % |
| --- | --- |
| $Li_2O$ | 34 |
| $SiO_2$ | 55 |
| $La_2O_3$ | 2 |
| $Ta_2O_5$ | 8 |
| $Cs_2O$ | 1 |

13. The glass composition of claim 1 consisting essentially of:

| Component | Mole % |
| --- | --- |
| $Li_2O$ | 40 |
| $SiO_2$ | 50 |
| $La_2O_3$ | 5 |
| $Ta_2O_5$ | 4 |
| $Cs_2O$ | 1 |

14. The glass composition of claim 1 consisting essentially of:

| Component | Mole % |
| --- | --- |
| $Li_2O$ | 32–36 |
| $SiO_2$ | 55–59 |
| $La_2O_3$ | 4–7 |
| $Ta_2O_5$ | 4–7 |
| $Cs_2O$ | 0–3 |

15. The glass composition of claim 14 consisting essentially of:

| Component | Mole % |
| --- | --- |
| $Li_2O$ | 34 |
| $SiO_2$ | 55 |
| $La_2O_3$ | 5 |
| $Ta_2O_5$ | 5 |
| $Cs_2O$ | 1 |

16. The glass composition of claim 14 consisting essentially of:

| Component | Mole % |
| --- | --- |
| $Li_2O$ | 33 |
| $SiO_2$ | 56 |
| $La_2O_3$ | 5 |

| Component | Mole % |
|---|---|
| $Ta_2O_5$ | 6 |

17. The glass composition of claim 14 consisting essentially of

| Component | Mole % |
|---|---|
| $Li_2O$ | 32 |
| $SiO_2$ | 57 |
| $La_2O_3$ | 5 |
| $Ta_2O_5$ | 6 |

18. The glass composition of claim 14 consisting essentially of:

| Component | Mole % |
|---|---|
| $Li_2O$ | 33 |
| $SiO_2$ | 56 |
| $La_2O_3$ | 4 |
| $Ta_2O_5$ | 7 |

19. The glass composition of claim 14 consisting essentially of:

| Component | Mole % |
|---|---|
| $Li_2O$ | 34 |
| $SiO_2$ | 55 |
| $La_2O_3$ | 6 |
| $Ta_2O_5$ | 5 |

20. The glass composition of claim 14 consisting essentially of:

| Component | Mole % |
|---|---|
| $Li_2O$ | 34 |
| $SiO_2$ | 55 |
| $La_2O_3$ | 5 |
| $Ta_2O_5$ | 6 |

21. The glass composition of claim 14 consisting essentially of:

| Component | Mole % |
|---|---|
| $Li_2O$ | 34 |
| $SiO_2$ | 55 |
| $La_2O_3$ | 4 |
| $Ta_2O_5$ | 7 |

22. The glass composition of claim 14 consisting essentially of:

| Component | Mole % |
|---|---|
| $Li_2O$ | 33 |
| $SiO_2$ | 56 |
| $La_2O_3$ | 6 |
| $Ta_2O_5$ | 4 |
| $Cs_2O$ | 1 |

23. The glass composition of claim 14 consisting essentially of:

| Component | Mole % |
|---|---|
| $Li_2O$ | 34 |
| $SiO_2$ | 55 |
| $La_2O_3$ | 3 |
| $Ta_2O_5$ | 5 |
| $Cs_2O$ | 3 |

24. The glass composition of claim 14, wherein said $La_2O_3$ and said $Ta_2O_5$ are present in said composition in approximately equal molar amounts.

25. The glass composition of claim 1, wherein said $La_2O_3$ and said $Ta_2O_5$ are present in said composition in approximately equal molar amounts.

26. A pH responsive glass membrane for use with electrodes for pH and potentiometric measurements, said glass membrane possessing a log volume resistivity at 25° C. within the range of about 8.3 and 9.5 ohm-centimeters, and having a composition consisting essentially of:

| Component | Mole % |
|---|---|
| $Li_2O$ | 30–40 |
| $SiO_2$ | 50–60 |
| $La_2O_3$ | 2–8 |
| $Ta_2O_5$ | 2–8 |
| $Cs_2O$ | 0–3 |
| Total $Li_2O + Ta_2O_5$ | 34 |

* * * * *

UNITED STATES PATENT AND TRADEMARK OFFICE
CERTIFICATE OF CORRECTION

PATENT NO. : 4,028,196
DATED : June 7, 1977
INVENTOR(S) : Chung-Chang Young

It is certified that error appears in the above-identified patent and that said Letters Patent are hereby corrected as shown below:

Col. 3, line 2, after "$Li_2O+Ta_2O_5$", insert -- $\geq$ --;

line 39, "ph" should read --pH--.

Col. 5, line 63, "of" should read --or--.

Col. 10, line 49, (Claim 26), in the second column under

"Mole %", the figure "34" should read

-- $\geq 34$ --.

Signed and Sealed this

Twenty-eighth Day of November 1978

[SEAL]

Attest:

RUTH C. MASON
Attesting Officer

DONALD W. BANNER
Commissioner of Patents and Trademarks